United States Patent
Kuisma et al.

(10) Patent No.: US 12,138,072 B2
(45) Date of Patent: Nov. 12, 2024

(54) APPARATUS AND METHOD FOR ENERGY EXPENDITURE ESTIMATION

(71) Applicants: LAPPEENRANNAN-LAHDEN TEKNILLINEN YLIOPISTO LUT, Lappeenranta (FI); JYVÄSKYLÄN YLIOPISTO, Jyväskylän yliopisto (FI)

(72) Inventors: Mikko Kuisma, Lappeenranta (FI); Antti Immonen, Lappeenranta (FI); Saku Levikari, Lappeenranta (FI); Heikki Peltonen, Muurame (FI); Esa Launis, Muurame (FI); Mika Silvennoinen, Jyväskylä (FI)

(73) Assignees: LAPPEENRANNAN-LAHDEN TEKNILLINEN YLIOPISTO LUT, Lappeenranta (FI); JYVÄSKYLÄN YLIOPISTO, Jyväskylän Yliopisto (FI)

( * ) Notice: Subject to any disclaimer, the term of this patent is extended or adjusted under 35 U.S.C. 154(b) by 346 days.

(21) Appl. No.: 17/762,542

(22) PCT Filed: Jun. 22, 2020

(86) PCT No.: PCT/FI2020/050444
§ 371 (c)(1),
(2) Date: Mar. 22, 2022

(87) PCT Pub. No.: WO2021/058854
PCT Pub. Date: Apr. 1, 2021

(65) Prior Publication Data
US 2022/0354424 A1    Nov. 10, 2022

(30) Foreign Application Priority Data
Sep. 23, 2019   (FI) .................... 20195796

(51) Int. Cl.
*A61B 5/00*     (2006.01)
*A61B 5/0205*   (2006.01)
(Continued)

(52) U.S. Cl.
CPC ........ *A61B 5/4866* (2013.01); *A61B 5/02055* (2013.01); *A61B 5/1114* (2013.01);
(Continued)

(58) Field of Classification Search
CPC . A61B 5/4866; A61B 5/02055; A61B 5/1114; A61B 5/1118; A61B 5/443;
(Continued)

(56) References Cited

U.S. PATENT DOCUMENTS

| | | | |
|---|---|---|---|
| 8,775,120 B2 * | 7/2014 | Molettiere | A63B 71/0686 |
| | | | 702/160 |
| 2012/0245439 A1 * | 9/2012 | Andre | A61B 5/0022 |
| | | | 600/595 |

(Continued)

FOREIGN PATENT DOCUMENTS

| | | |
|---|---|---|
| WO | 2009/131664 | 10/2009 |
| WO | 2010/077997 | 7/2010 |

(Continued)

OTHER PUBLICATIONS

International Application for PCT/FI2020/050444 mailed Oct. 5, 2020, 3 pages.

(Continued)

*Primary Examiner* — Jonathan T Kuo
(74) *Attorney, Agent, or Firm* — NIXON & VANDERHYE

(57) ABSTRACT

An apparatus for energy expenditure estimation includes a heart rate sensor for producing a heart rate value indicative of a heart rate of an individual, a heat-flux sensor for producing a heat-flux value indicative of a heat-flux flowing (Continued)

through a measurement area on the skin of the individual, and a processing system communicatively connected to the heart rate sensor and the heat-flux sensor. The processing system is configured to produce an estimate of the energy expenditure based on the heart rate value and the heat-flux value. The use of the heat-flux value improves the accuracy of the estimation especially during low-intensity exercise and rest, when both heart rate and acceleration values often fail to provide information meaningful enough for energy expenditure estimation.

17 Claims, 4 Drawing Sheets

(51) Int. Cl.
*A61B 5/024* (2006.01)
*A61B 5/11* (2006.01)
(52) U.S. Cl.
CPC ............ *A61B 5/1118* (2013.01); *A61B 5/443* (2013.01); *A61B 5/4869* (2013.01); *A61B 5/7264* (2013.01); *A61B 5/7278* (2013.01); *A61B 5/024* (2013.01); *A61B 2560/0252* (2013.01); *A61B 2560/0257* (2013.01); *A61B 2562/0271* (2013.01); *A61B 2562/029* (2013.01)
(58) Field of Classification Search
CPC ... A61B 5/4869; A61B 5/7264; A61B 5/7278; A61B 5/024; A61B 2560/0252; A61B 2560/0257; A61B 2562/0271; A61B 2562/029; A61B 5/02438; A61B 5/681; A61B 5/6824; A61B 5/6829; A61B 5/01; A61B 5/02416; A61B 5/0533; A61B 2560/0242; A61B 5/11; A61B 5/1123; A61B 5/222; G01K 17/00; G16H 50/00–50/80
See application file for complete search history.

(56) References Cited

U.S. PATENT DOCUMENTS

| 2014/0163927 | A1* | 6/2014 | Molettiere | ............ A61B 5/1112 |
| | | | | 702/189 |
| 2014/0275852 | A1 | 9/2014 | Hong et al. | |
| 2017/0337349 | A1* | 11/2017 | Cronin | ................. A61B 5/4866 |
| 2018/0078202 | A1* | 3/2018 | DeGroot | ............... A61B 5/1118 |

FOREIGN PATENT DOCUMENTS

| WO | 2011/032016 | 3/2011 |
| WO | 2016/087381 | 6/2016 |

OTHER PUBLICATIONS

Written Opinion of the ISA for PCT/FI2020/050444 mailed Oct. 5, 2020, 5 pages.
Search Report for FI20195796 dated Mar. 10, 2020, 2 pages.

* cited by examiner ated device is not worn by a user, and in a normal power state when the control unit determines that the wearable fitness monitoring device is worn by a user. The wearable fitness monitoring device described in U.S. Pat. No. 8,920,332 can be for example a smart wrist device.

APPARATUS AND METHOD FOR ENERGY EXPENDITURE ESTIMATION

This application is the U.S. national phase of International Application No. PCT/FI2020/050444 filed Jun. 22, 2020 which designated the U.S. and claims priority to FI 20195796 filed Sep. 23, 2019, the entire contents of each of which are hereby incorporated by reference.

TECHNICAL FIELD

The disclosure relates to a method and an apparatus for estimating energy expenditure of an individual. Furthermore, the disclosure relates to a computer program for estimating energy expenditure of an individual.

BACKGROUND

A human or animal body expends energy while participating in physical activities as well as just resting. Energy is expended for basal metabolism and for physical activities. In many cases, there is a need to measure or estimate the energy expenditure "EE" of a human or animal body in order to monitor for example a daily calorie consumption. Portable devices such as e.g. smart watches have become popular tools for estimating the energy expenditure. These devices typically measure heart rate and movement e.g. acceleration, and thereafter calculate an estimate for the energy expenditure based on these quantities. Publication U.S. Pat. No. 8,920,332 describes a wearable fitness monitoring device that comprises a motion sensor and a photoplethysmographic "PPG" sensor. The PPG sensor includes a periodic light source, a photodetector, and a circuitry determining a heart rate based on an output of the photodetector. The wearable fitness monitoring device described in U.S. Pat. No. 8,920,332 can be provided with means for operating the wearable fitness monitoring device in a low power state when a control unit of the wearable fitness monitoring device determines that the wearable fitness monitoring device is not worn by a user, and in a normal power state when the control unit determines that the wearable fitness monitoring device is worn by a user. The wearable fitness monitoring device described in U.S. Pat. No. 8,920,332 can be for example a smart wrist device.

While data indicative of movement e.g. acceleration does not provide direct information about the energy expenditure, the heart rate correlates well with the energy expenditure, especially during moderate and high-intensity exercises. However, most of peoples' daily activities consist of low-level activities and/or rest. Therefore, heart rate and movement-based energy expenditure estimates are often inaccurate outside moderate and high-intensity physical exercises. Thus, there is still a need for new technologies for estimating the energy expenditure.

SUMMARY

The following presents a simplified summary in order to provide a basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to a more detailed description of exemplifying embodiments of the invention.

In accordance with the invention, there is provided a new apparatus for energy expenditure estimation. An apparatus according to the invention comprises:
  a heart rate sensor for producing a heart rate value indicative of a heart rate of an individual,
  a heat-flux sensor for producing a heat-flux value indicative of a heat-flux flowing through a measurement area on a skin of the individual, and
  a processing system communicatively connected to the heart rate sensor and to the heat-flux sensor and configured to produce an estimate of the energy expenditure based on the heart rate value and the heat-flux value.

The use of the above-mentioned heat-flux value improves the accuracy of the energy expenditure estimation especially during low-intensity exercises and rest, when the heart rate and e.g. acceleration data often fail to provide information meaningful enough for energy expenditure estimation.

In accordance with the invention, there is provided also a new method for energy expenditure estimation. A method according to the invention comprises:
  measuring a heart rate of an individual,
  measuring a heat-flux flowing through a measurement area on a skin of the individual, and
  producing an estimate of the energy expenditure based on the measured heart rate and the heat-flux.

In accordance with the invention, there is provided also a new computer program for energy expenditure estimation. A computer program according to the invention comprises computer executable instructions for controlling a programmable processor to:
  receive, from a heart rate sensor, a heart rate value indicative of a heart rate of an individual,
  receive, from a heat-flux sensor, a heat-flux value indicative of a heat-flux flowing through a measurement area on a skin of the individual, and
  produce an estimate of the energy expenditure based on the received heart rate value and the heat-flux value.

In accordance with the invention, there is provided also a new computer program product. The computer program product comprises a non-volatile computer readable medium, e.g. a compact disc "CD", encoded with a computer program according to the invention.

Exemplifying and non-limiting embodiments are described in accompanied dependent claims.

Various exemplifying and non-limiting embodiments both as to constructions and to methods of operation, together with additional objects and advantages thereof, will be best understood from the following description of specific exemplifying and non-limiting embodiments when read in conjunction with the accompanying drawings.

The verbs "to comprise" and "to include" are used in this document as open limitations that neither exclude nor require the existence of unrecited features. The features recited in dependent claims are mutually freely combinable unless otherwise explicitly stated. Furthermore, it is to be understood that the use of "a" or "an", i.e. a singular form, throughout this document does not exclude a plurality.

BRIEF DESCRIPTION OF THE FIGURES

Exemplifying and non-limiting embodiments and their advantages are explained in greater detail below in the sense of examples and with reference to the accompanying drawings, in which.

DESCRIPTION OF THE EXEMPLIFYING EMBODIMENTS

The specific examples provided in the description below should not be construed as limiting the scope and/or the applicability of the accompanied claims. Lists and groups of examples provided in the description are not exhaustive unless otherwise explicitly stated.

Figure 1:
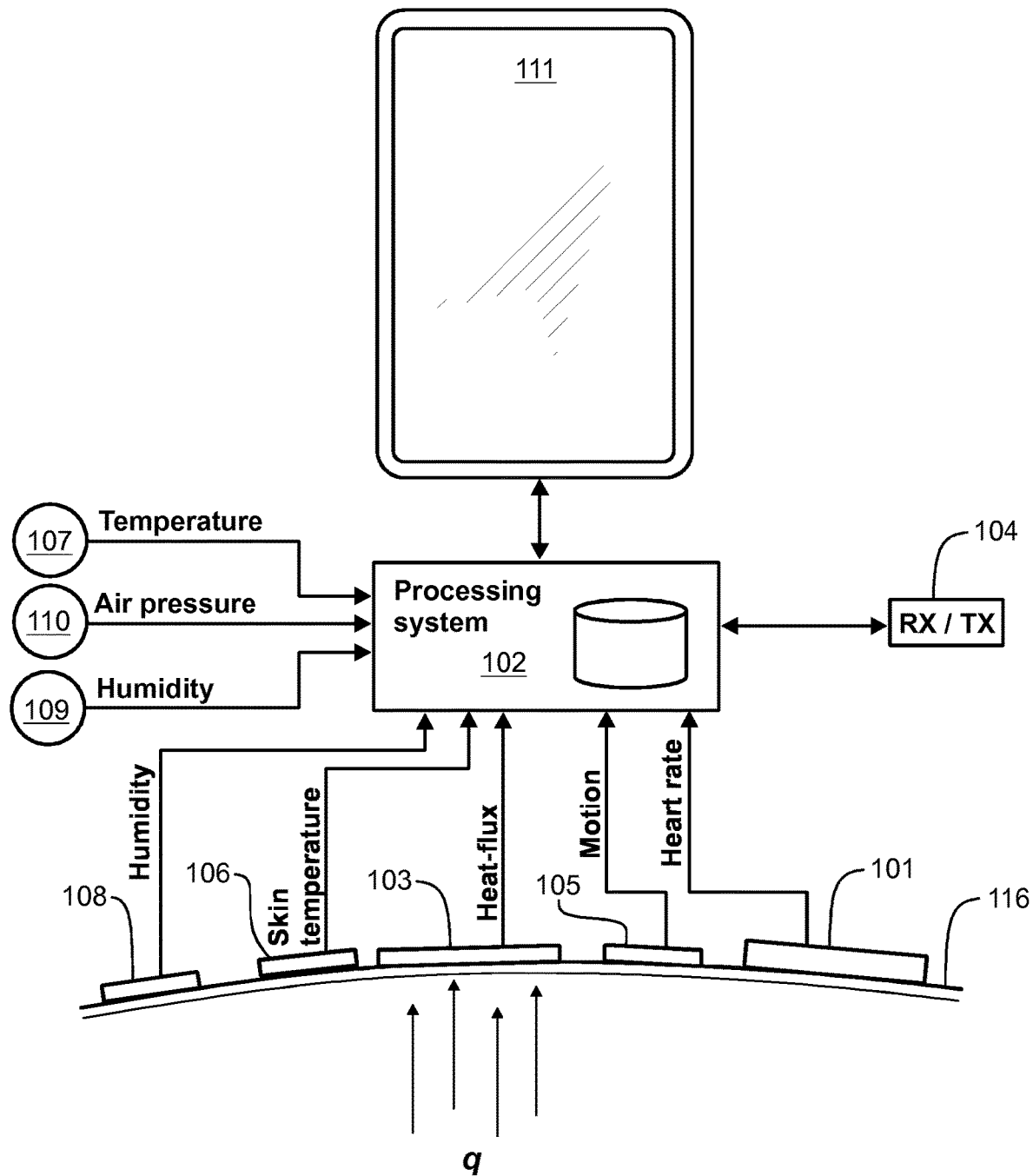
FIG. 1 shows a functional block diagram of an apparatus according to an exemplifying and non-limiting embodiment for energy expenditure estimation.

FIG. 1 shows a functional block diagram of an apparatus according to an exemplifying and non-limiting embodiment for energy expenditure estimation. The apparatus comprises a heart rate sensor 101 for producing a heart rate value indicative of a heart rate of an individual. The heart rate sensor 101 can be for example a photoplethysmographic "PPG" sensor or another suitable sensor for measuring the heart rate. The apparatus comprises a heat-flux sensor 103 for producing a heat-flux value indicative of a heat-flux q flowing through a measurement area on a skin 116 of the individual. The apparatus comprises a processing system 102 that is communicatively connected to the heart rate sensor 101 and to the heat-flux sensor 103. The processing system 102 is configured to produce an estimate of the energy expenditure "EE" of the individual based on the above-mentioned heart rate value and the heat-flux value. The use of the heat-flux value improves the accuracy of the energy expenditure estimation especially during low-intensity exercises and rest, when the heart rate and e.g. acceleration data often fail to provide information meaningful enough for energy expenditure estimation. In this exemplifying case, the apparatus further comprises a user interface 111 that may comprise for example a touch screen.

The heat-flux sensor 103 can be any suitable heat-flux sensor for measuring the heat-flux q flowing through the skin 116. For example, the heat-flux sensor 103 can be based on multiple thermoelectric junctions so that tens, hundreds, or even thousands of thermoelectric junctions are connected in series. For another example, the heat-flux sensor 103 can be based on one or more anisotropic elements where electromotive force is created from a heat-flux by the Seebeck effect. The anisotropy can be implemented with suitable anisotropic material such as for example single-crystal bismuth. Another option for implementing the anisotropy is a multilayer structure where layers are oblique with respect to a surface of the heat-flux sensor for receiving the heat-flux.

In an apparatus according to an exemplifying and non-limiting embodiment, the processing system 102 is configured to estimate the energy expenditure EE according to the formula:

$$EE=f(HR,HF),$$

where HR is the heart rate value, HF is the heat-flux value, and f is a function that expresses the energy expenditure EE as a function of the heart rate value HR and the heat-flux value HF. The function f can be constructed based on for example empirical data and/or theoretical models. The function f can be implemented for example as a lookup table or as a mathematical formula. The empirical data for constructing the function f can be obtained e.g. by means of indirect calorimetry, such as respiratory gas analysis; or by means of direct calorimetry, such as room calorimeter.

In an apparatus according to an exemplifying and non-limiting embodiment, the processing system 102 is configured to estimate the energy expenditure EE according to the formula:

$$EE=f_S(W_{HR}HR+W_{HF}HF),$$

where $W_{HR}$ is a weight factor of the heart rate, $W_{HF}$ is a weight factor of the heat-flux, and $f_S$ is a function that expresses the energy expenditure EE as a function of a weighted sum of the heart rate value HR and the heat-flux value HF. The function $f_S$ can be constructed based on for example empirical data and/or theoretical models. The function $f_S$ can be implemented for example as a lookup table or as a mathematical formula. The processing system 102 is configured to increase a relative weight of the heart rate on the estimate of the energy expenditure EE with respect to a relative weight of the heat-flux on the estimate of the energy expenditure EE in response to an increase of the heart rate value HR. In other words, the weight factor $W_{HR}$ is increased with respect to the weight factor $W_{HF}$ when the heart rate value HR increases. As the heart rate correlates well with the energy expenditure EE during a high-intensity exercise i.e. when the heart rate is high, the relative weight of the heart rate on the estimate of the energy expenditure EE is advantageously higher than the relative weight of the heat-flux during the high-intensity exercise. On the other hand, as the heat-flux is a better quantity for estimating the energy expenditure EE at rest and during a low physical load, the weight factor $W_{HR}$ is advantageously decreased with respect to the weight factor $W_{HF}$ when the heart rate value HR decreases.

In an apparatus according to an exemplifying and non-limiting embodiment, the processing system 102 is configured to produce the estimate of the energy expenditure EE based on the heart rate value HR, the heat-flux value HF, and one or more of the following first quantities:

activity data descriptive of physical activity of the individual during measurements of the heart rate and the heat-flux, a skin temperature value indicative of a local temperature of the skin of the individual, an ambient temperature value indicative of temperature of ambient air surrounding the individual a humidity value indicative of local humidity of air at a humidity measurement place belonging to a near-area less than a predetermined distance from the skin of the individual, a skin moisture value indicative of moisture of the skin of the individual, an ambient humidity value indicative of humidity of air outside the near-area, and a barometric pressure value indicative of pressure of ambient air surrounding the individual.

A function, e.g. a lookup table or a mathematical formula, for expressing the estimate of the energy expenditure EE as a function of the heart rate value HR, the heat-flux value HF, and one or more of the above-mentioned first quantities can be constructed with the aid of for example empirical data and/or theoretical models.

The exemplifying apparatus illustrated in FIG. 1 comprises at least one movement sensor 105 for producing at least one movement value indicative of movement of at least one part, e.g. a hand or a foot, of the body of the individual. The processing system 102 is configured to produce the above-mentioned activity data based on the at least one movement value. The movement sensor 105 can be for example a wrist-worn three dimensional "3D" accelerometer, and the processing system 102 can be configured to use the acceleration information to classify the current activity type.

The exemplifying apparatus illustrated in FIG. 1 comprises a temperature sensor 106 for producing the above-mentioned skin temperature value, a temperature sensor 107 for producing the above-mentioned ambient temperature value, a humidity sensor 108 for producing the above-mentioned humidity value indicative of the air humidity in the near-area of the skin, a humidity sensor 109 for producing the above-mentioned ambient humidity value, and a pressure sensor 110 for producing the above-mentioned barometric pressure value. Furthermore, the exemplifying apparatus illustrated in FIG. 1 may comprise a skin moisture sensor for producing the above-mentioned skin moisture value indicative of moisture of the skin of the individual. The skin moisture sensor may comprise e.g. means for measuring a galvanic skin resistance "GSR". The skin moisture sensor can be e.g. integrated with the temperature sensor 106 or it can be a separate device.

It is also possible that the processing system 102 is configured to receive one or more of the above-mentioned first quantities via a data interface 104 from an external system or device.

In an apparatus according to an exemplifying and non-limiting embodiment, the processing system 102 is configured to produce the estimate of the energy expenditure EE based on the heart rate value HR, the heat-flux value HF, one or more of the above-mentioned first quantities and/or one or more of the following second quantities:
- the body mass of the individual,
- the height of the individual,
- the sex of the individual,
- the age of the individual,
- the activity of the lifestyle of the individual, e.g. an integer ranging from 1 to 10 so that 1=sedentary and 10=athlete.

A function, e.g. a lookup table or a mathematical formula, for expressing the estimate of the energy expenditure EE as a function of the heart rate value HR, the heat-flux value HF, and one or more of the above-mentioned first quantities and/or one or more of the above-mentioned second quantities can be constructed with the aid of for example empirical data and/or theoretical models.

In an apparatus according to an exemplifying and non-limiting embodiment, the processing system 102 is configured to constitute a recurrent neural network for producing a first preliminary result PR1 based on at least the heart rate value HR and the heat-flux value HF, and one or more densely connected neural networks for producing the estimate of the energy expenditure EE based on at least the first preliminary result PR1.

In an apparatus according to an exemplifying and non-limiting embodiment, the recurrent neural network is configured to produce the first preliminary PR1 result based on the heart rate value HR, the heat-flux value HF, and at least one of the following first quantities: activity data descriptive of physical activity of the individual during measurements of the heart rate and the heat-flux, one or more skin temperature values indicative of one or more local temperatures of the skin of the individual, an ambient temperature value indicative of temperature of ambient air surrounding the individual, one or more humidity values indicative of local humidity of air at one or more humidity measurement places belonging to a near-area less than a predetermined distance from the skin of the individual, an ambient humidity value indicative of humidity of air outside the near-area, and a barometric pressure value indicative of pressure of the ambient air.

In an apparatus according to an exemplifying and non-limiting embodiment, a first one of the densely connected neural networks is configured to produce a second preliminary result PR2 based on individual-related data, and a second one of the densely connected neural networks is configured to produce a third preliminary result PR3 based on a combination, e.g. a concatenation, of the first and second preliminary results PR1 and PR2. The individual-related data is indicative of at least one of the following second quantities: the body mass of the individual, the height of the individual, the sex of the individual, the age of the individual, the activity of the lifestyle of the individual. The processing system 102 can be configured to constitute a neuron implementing a scalar-valued function of a vector-valued argument for producing the estimate of the energy expenditure EE based on the third preliminary result PR3.

Training data for the above-mentioned neural networks can be constructed from input and target data arranged as a time series. The input data comprises values of the heart rate and the heat-flux. Furthermore, the input data may comprise values of one or more of the above-mentioned first quantities and/or values of one or more of the above-mentioned second quantities. The target data comprises values of the energy expenditure EE measured e.g. by means of indirect calorimetry, such as respiratory gas analysis, or by means of direct calorimetry, such as room calorimeter. Each input-target pair of the time series comprises data collected from an individual during a measurement run. The time series may comprise the entire measurement run, or windowed sections of the measurement run, possibly overlapped. The above-mentioned neural networks are trained with the above-described training data. After the neural networks have been trained, the energy expenditure EE can be estimated without a need for a calorimetric measurement.

The processing system 102 of the apparatus illustrated in FIG. 1 can be implemented for example with one or more processor circuits each of which can be a programmable processor circuit provided with appropriate software, a dedicated hardware processor such as for example an application specific integrated circuit "ASIC", or a configurable hardware processor such as for example a field programmable gate array "FPGA". Furthermore, the processing system 102 may comprise one or more memory circuits each of which can be for example a random-access memory "RAM" circuit.

Figure 2:
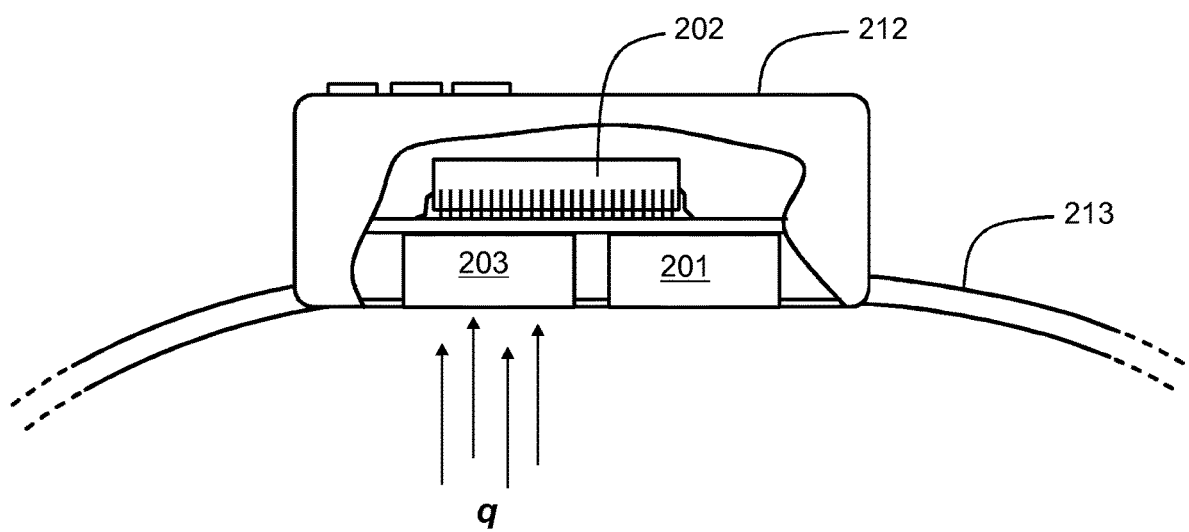
FIG. 2 illustrates schematically an apparatus according to an exemplifying and non-limiting embodiment for energy expenditure estimation.

FIG. 2 illustrates schematically an apparatus according to an exemplifying and non-limiting embodiment for energy expenditure estimation. In this exemplifying case, the apparatus is a portable device which comprises a fastening band 213 that can be for example a wrist band, a chest band, a strap, or a belt. In FIG. 2, a casing 212 of the apparatus is presented as a partial section view. The apparatus comprises a heart rate sensor 201, a heat-flux sensor 203, and a processing system 202 communicatively connected to the heart rate sensor 201 and to the heat-flux sensor 203. The heart rate sensor 201 is configured to produce a heart rate value indicative of a heart rate of an individual, and the heat-flux sensor 203 is configured to produce a heat-flux value indicative of a heat-flux q flowing through a measurement area on the skin of the individual. The processing system 202 is configured to produce an estimate of energy expenditure of the individual based on at least the heart rate value and the heat-flux value.

Figure 3:
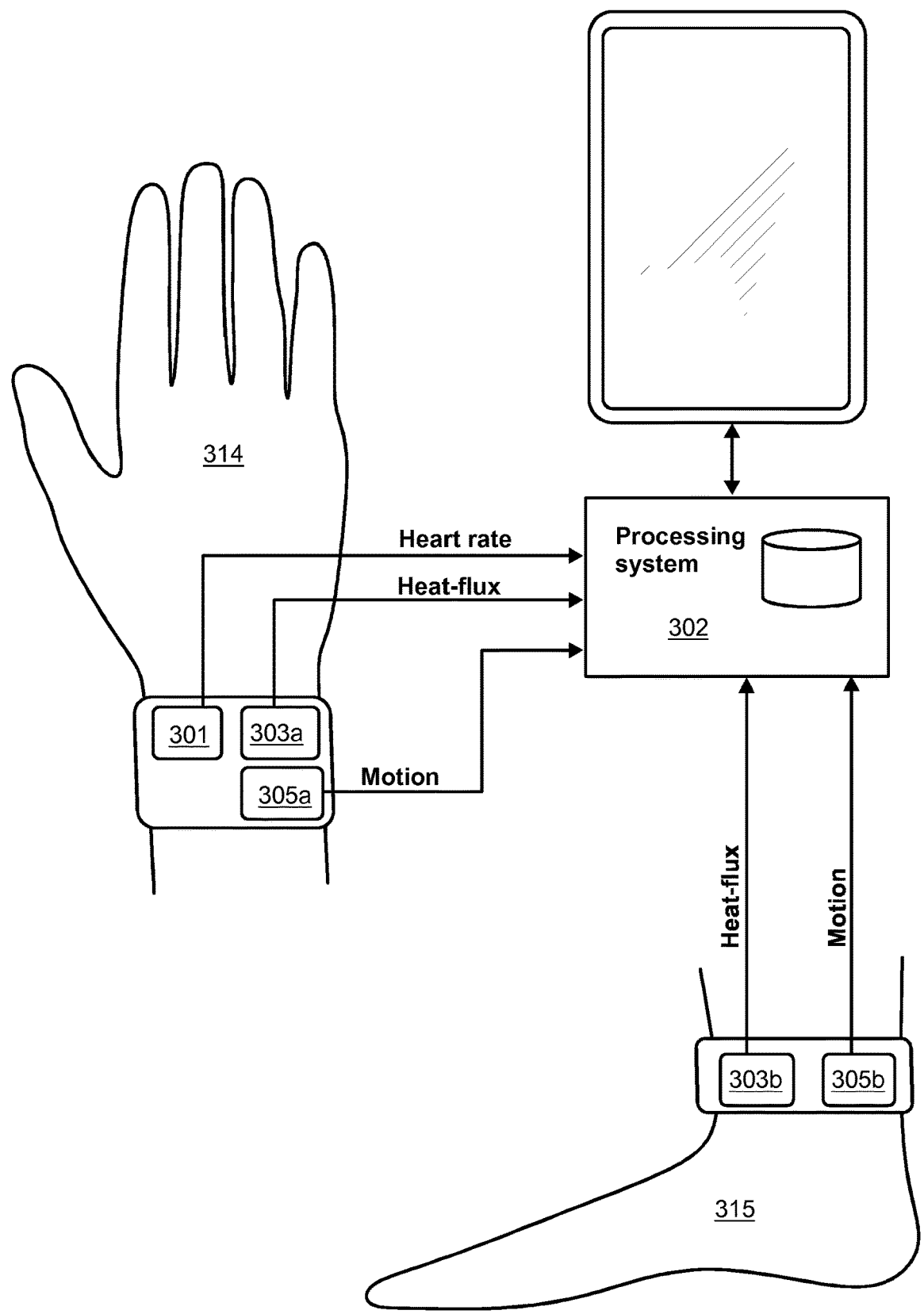
FIG. 3 shows a functional block diagram of an apparatus according to an exemplifying and non-limiting embodiment for energy expenditure estimation.

FIG. 3 shows a functional block diagram of an apparatus according to an exemplifying and non-limiting embodiment for energy expenditure estimation. The apparatus comprises a heart rate sensor 201 for producing a heart rate value indicative of a heart rate of an individual. The apparatus comprises two heat-flux sensors 303a and 303b for producing heat-flux values indicative of heat-fluxes flowing through two measurement areas on the skin of the individual. In the exemplifying situation shown in FIG. 3, the heat-flux sensor 303a is placed on a wrist of the individual and the heat-flux sensor 303b is placed on an ankle of the individual. In this exemplifying case, the apparatus comprises two movement sensors 305a and 305b for producing movement values indicative of movements of a hand 314 and a foot 315 of the individual. The movement sensors 305a and 305b can be e.g. acceleration sensors. The apparatus comprises a processing system 302 for producing an estimate of energy expenditure of the individual based on the heart rate value, the heat-flux values, and the movement values.

In an apparatus according to an exemplifying and non-limiting embodiment, the processing system 302 is configured to weight the heat-flux value produced by the heat-flux sensor 303a more than the heat-flux value produced by the heat-flux sensor 303b in response to a situation in which the movement sensor 305a indicates more movement than the movement sensor 305b. Correspondingly, the processing system 302 is configured to weight the heat-flux value produced by the heat-flux sensor 303b more than the heat-flux value produced by the heat-flux sensor 303a in response to a situation in which the movement sensor 305b indicates more movement than the movement sensor 305a. The estimate of the energy expenditure can be for example a weighted average of preliminary estimates each being based on a respective one of the heat-flux values. A weight factor of the preliminary estimate related to a more intensive movement is set to be greater than the weight factor of the other preliminary estimate related to a less intensive movement. Thus, a heat-flux value which is in a closer relation to physical activity is weighted more than the other heat flux value.

It is worth noting that an apparatus according to an exemplifying and non-limiting embodiment may comprise three or more heat-flux sensors for producing heat-flux values indicative of heat-fluxes flowing through three or more measurement areas on the skin of an individual. Correspondingly, an apparatus according to an exemplifying and non-limiting embodiment may comprise three or more movement sensors.

Figure 4:
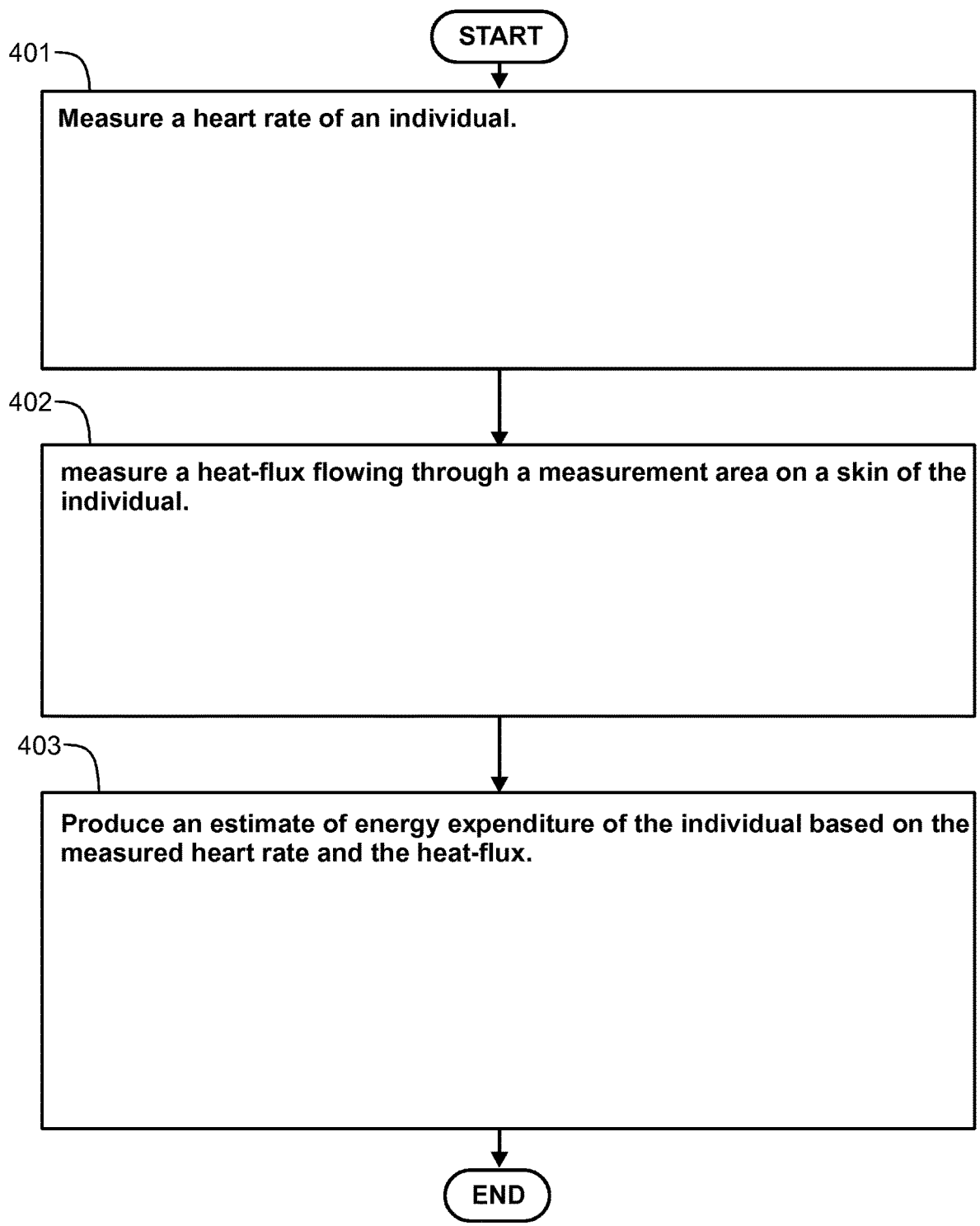
FIG. 4 shows a flowchart of a method according to an exemplifying and non-limiting embodiment for energy expenditure estimation.

FIG. 4 shows a flowchart of a method according to an exemplifying and non-limiting embodiment for energy expenditure estimation. The method comprises the following actions:
- action 401: measuring a heart rate of an individual,
- action 402: measuring a heat-flux flowing through a measurement area on a skin of the individual, and
- action 403: producing an estimate of the energy expenditure based on the measured heart rate and the heat-flux.

A method according to an exemplifying and non-limiting embodiment comprises increasing a relative weight of the measured heart rate on the estimate of the energy expenditure with respect to a relative weight of the measured heat-flux on the estimate of the energy expenditure in response to an increase of the heart rate.

In a method according to an exemplifying and non-limiting embodiment, the estimate of the energy expenditure is produced based on the measured heart rate, the measured heat-flux, and activity data descriptive of physical activity of the individual during the measuring the heart rate and the heat-flux.

A method according to an exemplifying and non-limiting embodiment comprises measuring movement of at least one part of the body of the individual and producing the activity data based on the measured movement.

A method according to an exemplifying and non-limiting embodiment comprises:
- measuring at least two heat-fluxes flowing through at least two measurement areas on the skin of the individual,
- measuring movements of at least two parts of a body of the individual, and
- weighting, in the producing the estimate of the energy expenditure, a first one of the measured heat-fluxes more than a second one of the measured heat-fluxes in response to a situation in which the measured movements indicate more movement on the measurement area related to the first one of the measured heat-fluxes than on the measurement area related to the second one of the measured heat-fluxes.

A method according to an exemplifying and non-limiting embodiment comprises measuring one or more local temperatures of the skin of the individual and using the measured one or more local temperatures in the producing the estimate of the energy expenditure.

A method according to an exemplifying and non-limiting embodiment comprises using, in the producing the estimate of the energy expenditure, an ambient temperature value indicative of temperature of the ambient air surrounding the individual.

A method according to an exemplifying and non-limiting embodiment comprises measuring one or more humidity values indicative of local humidity of air at one or more humidity measurement places belonging to a near-area less than a predetermined distance from the skin of the individual and using the one or more humidity values in the producing the estimate of the energy expenditure.

A method according to an exemplifying and non-limiting embodiment comprises measuring one or more skin moisture values indicative of moisture of the skin of the individual at one or more measurement places on the skin of the individual, and using the one or more skin moisture values in the producing the estimate of the energy expenditure.

A method according to an exemplifying and non-limiting embodiment comprises using, in the producing the estimate of the energy expenditure, an ambient humidity value indicative of humidity of air outside the above-mentioned near-area.

A method according to an exemplifying and non-limiting embodiment comprises using, in the producing the estimate of the energy expenditure, a barometric pressure value indicative of pressure of ambient air surrounding the individual.

A method according to an exemplifying and non-limiting embodiment comprises using, in the producing the estimate of the energy expenditure, individual-related data indicative of at least one of the following: the body mass of the individual, the height of the individual, the sex of the individual, the age of the individual, activity of the lifestyle of the individual.

A method according to an exemplifying and non-limiting embodiment comprises producing a first preliminary result by supplying at least the measured heart rate and the measured heat-flux to a recurrent neural network and producing the estimate of the energy expenditure by supplying at least the first preliminary result to one or more densely connected neural networks.

In a method according to an exemplifying and non-limiting embodiment, the above-mentioned first preliminary result is produced by supplying, to the recurrent neural network, the measured heart rate, the measured heat-flux, and at least one of the following: activity data descriptive of physical activity of the individual during the measuring the heart rate and the heat-flux, one or more local temperatures measured on the skin of the individual, temperature of the ambient air surrounding the individual, one or more humidity values indicative of local humidity of air at one or more humidity measurement places belonging to a near-area less than a predetermined distance from the skin of the individual, humidity of air outside the near-area, and/or pressure of the ambient air.

A method according to an exemplifying and non-limiting embodiment comprises producing a second preliminary result by supplying individual-related data to a first one of the densely connected neural networks, producing a third preliminary result by supplying a combination of the first and second preliminary results to a second one of the densely connected neural networks, and producing the estimate of the energy expenditure by supplying the third preliminary result to a neuron implementing a scalar-valued function of a vector valued argument. The above-mentioned individual-related data is indicative of at least one of the following: the body mass of the individual, the height of the individual, the sex of the individual, the age of the individual, and/or activity of the lifestyle of the individual.

A computer program according to an exemplifying and non-limiting embodiment comprises computer executable instructions for controlling a programmable processor to carry out actions related to a method according to any of the above-described exemplifying embodiments.

A computer program according to an exemplifying and non-limiting embodiment comprises software modules for energy expenditure estimation. The software modules comprise computer executable instructions for controlling a programmable processor to:
receive, from a heart rate sensor, a heart rate value indicative of a heart rate of an individual,
receive, from a heat-flux sensor, a heat-flux value indicative of a heat-flux flowing through a measurement area on a skin of the individual, and
produce an estimate of the energy expenditure based on the received heart rate value and the heat-flux value.

The above-mentioned software modules can be e.g. sub-routines or functions implemented with a suitable programming language.

A computer program product according to an exemplifying and non-limiting embodiment comprises a computer readable medium, e.g. a compact disc "CD", encoded with a computer program according to an embodiment of invention.

A signal according to an exemplifying and non-limiting embodiment is encoded to carry information defining a computer program according to an embodiment of invention. In this exemplifying case, the computer program can be downloadable from a server that may constitute e.g. a part of a cloud service.

The specific examples provided in the description given above should not be construed as limiting the applicability and/or interpretation of the appended claims. It is to be noted that lists and groups of examples given in this document are non-exhaustive lists and groups unless otherwise explicitly stated.

What is claimed is:

1. An apparatus for energy expenditure estimation, the apparatus comprising:
   a heart rate sensor configured to produce a heart rate value indicative of a heart rate of an individual, and
   a processing system communicatively connected to the heart rate sensor,
   wherein the apparatus further comprises a heat-flux sensor configured to produce a heat-flux value indicative of a heat-flux flowing through a measurement area on a skin of the individual, wherein the processing system is communicatively connected to the heat-flux sensor and configured to produce an estimate of the energy expenditure based on the heart rate value and the heat-flux value, and
   wherein the processing system is configured to increase a relative weight of the heart rate value on the estimate of the energy expenditure with respect to a relative weight of the heat-flux value on the estimate of the energy expenditure in response to an increase of the heart rate.

2. An apparatus according to claim 1, wherein the processing system is configured to produce the estimate of the energy expenditure based on the heart rate value, the heat-flux value, and activity data descriptive of physical activity of the individual during measurements of the heart rate and the heat-flux.

3. An apparatus according to claim 2, wherein the apparatus comprises at least one movement sensor for producing at least one movement value indicative of movement of at least one part of a body of the individual, and the processing system is configured to produce the activity data based on the at least one movement value.

4. An apparatus according to claim 1, wherein:
   the heat-flux sensor is one of at least two heat-flux sensors of the apparatus for producing heat-flux values indicative of heat-fluxes flowing through at least two measurement areas on the skin of the individual,
   the apparatus comprises at least two movement sensors for producing movement values indicative of movements of at least two parts of a body of the individual, and
   the processing system is configured to weight a first one of the heat-flux values more than a second one of the heat-flux values for producing the estimate of the energy expenditure in response to a situation in which the movement values indicate more movement on the measurement area related to the first one of the heat-flux values than on the measurement area related to the second one of the heat-flux values.

5. An apparatus according to claim 1, wherein the apparatus comprises at least one temperature sensor for producing a skin temperature value indicative of a local temperature of the skin of the individual, and the processing system is configured to use the skin temperature value for producing the estimate of the energy expenditure.

6. An apparatus according to claim 1, wherein the processing system is configured to use, for producing the estimate of the energy expenditure, an ambient temperature value indicative of temperature of ambient air surrounding the individual.

7. An apparatus according to claim 1, wherein the apparatus comprises at least one humidity sensor for producing a humidity value indicative of local humidity of air at a humidity measurement place belonging to a near-area less than a predetermined distance from the skin of the individual, and the processing system is configured to use the humidity value for producing the estimate of the energy expenditure.

8. An apparatus according to claim 1, wherein the apparatus comprises at least one skin moisture sensor for producing a skin moisture value indicative of moisture of the skin of the individual, and the processing system is configured to use the skin moisture value for producing the estimate of the energy expenditure.

9. An apparatus according to claim 1, wherein the processing system is configured to use, for producing the estimate of the energy expenditure, an ambient humidity value indicative of humidity of ambient air surrounding the individual.

10. An apparatus according to claim 1, wherein the processing system is configured to use, for producing the estimate of the energy expenditure, a barometric pressure value indicative of pressure of ambient air surrounding the individual.

11. An apparatus according to claim 1, wherein the processing system is configured to use, for producing the estimate of the energy expenditure, individual-related data indicative of at least one of the following: body mass of the individual, height of the individual, sex of the individual, age of the individual, activity of lifestyle of the individual.

12. An apparatus according to claim 1, wherein the processing system is configured to constitute a recurrent neural network for producing a first preliminary result based on at least the heart rate value and the heat-flux value and one or more densely connected neural networks for producing the estimate of the energy expenditure based on at least the first preliminary result.

13. An apparatus according to claim 12, wherein the recurrent neural network is configured to produce the first preliminary result based on the heart rate value, the heat-flux value, and at least one of the following: activity data descriptive of physical activity of the individual during measurements of the heart rate and the heat-flux, a skin temperature value indicative of a local temperature of the skin of the individual, an ambient temperature value indicative of temperature of ambient air surrounding the individual, one or more humidity values indicative of local humidity of air at one or more humidity measurement places belonging to a near-area less than a predetermined distance from the skin of the individual, an ambient humidity value indicative of humidity of air outside the near-area, a barometric pressure value indicative of pressure of the ambient air.

14. An apparatus according to claim 13, wherein a first one of the densely connected neural networks is configured to produce a second preliminary result based on individual-related data, and a second one of the densely connected neural networks is configured to produce a third preliminary result based on a combination of the first and second preliminary results, and the processing system is configured to constitute a neuron implementing a scalar-valued function of a vector-valued argument for producing the estimate of the energy expenditure based on the third preliminary result, the individual-related data being indicative of at least one of the following: body mass of the individual, height of the individual, sex of the individual, age of the individual, activity of lifestyle of the individual.

15. An apparatus according to claim 12, wherein a first one of the densely connected neural networks is configured to produce a second preliminary result based on individual-related data, and a second one of the densely connected neural networks is configured to produce a third preliminary result based on a combination of the first and second preliminary results, and the processing system is configured to constitute a neuron implementing a scalar-valued function of a vector-valued argument for producing the estimate of the energy expenditure based on the third preliminary result, the individual-related data being indicative of at least one of the following: body mass of the individual, height of the individual, sex of the individual, age of the individual, activity of lifestyle of the individual.

16. A method for energy expenditure estimation, the method comprising:
   measuring a heart rate of an individual,
   measuring a heat-flux flowing through a measurement area on a skin of the individual,
   producing an estimate of the energy expenditure based on the measured heart rate and the measured heat-flux, and
   increasing a relative weight of the measured heart rate on the estimate of the energy expenditure with respect to a relative weight of the measured heat-flux on the estimate of the energy expenditure in response to an increase of the heart rate.

17. A non-transitory computer readable medium encoded with a computer program for energy expenditure estimation, the computer program comprising computer executable instructions for controlling a programmable processor to:
   receive, from a heart rate sensor, a heart rate value indicative of a heart rate of an individual,
   receive, from a heat-flux sensor, a heat-flux value indicative of a heat-flux flowing through a measurement area on a skin of the individual,
   produce an estimate of the energy expenditure based on the received heart rate value and the received heat-flux value, and
   increase a relative weight of the measured heart rate on the estimate of the energy expenditure with respect to a relative weight of the measured heat-flux on the estimate of the energy expenditure in response to an increase of the heart rate.

* * * * *